(12) United States Patent
Fricker et al.

(10) Patent No.: US 6,325,968 B1
(45) Date of Patent: *Dec. 4, 2001

(54) ANTIMICROBIAL COMPOSITION DELIVERY SYSTEM WITH AN INTEGRATED FILLER

(75) Inventors: Christopher M. Fricker, Mentor, OH (US); Todd A. Christopher, New Palestine, IN (US); Brian E. Schindly, Mentor, OH (US); Karen Thomas, Eastlake, OH (US); David E. Minerovic, Concord, OH (US); Michael F. Jusek, Cleveland, OH (US)

(73) Assignee: Steris Corporation, Mentor, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/221,019

(22) Filed: Dec. 23, 1998

Related U.S. Application Data

(60) Provisional application No. 60/070,930, filed on Dec. 23, 1997.

(51) Int. Cl.[7] .......................................................... A61L 2/00
(52) U.S. Cl. .............................................................. 422/28
(58) Field of Search .......................... 422/1, 28, 263–264, 422/266, 275, 277, 278, 292

(56) References Cited

U.S. PATENT DOCUMENTS

| | | | |
|---|---|---|---|
| 1,072,351 | * 9/1913 | Munson | 422/292 |
| 2,494,456 | * 1/1950 | Still | 128/272 |
| 4,482,047 | 11/1984 | Ackermann et al. | |
| 4,483,439 | * 11/1984 | Steigerwald et al. | 206/219 |
| 4,779,722 | 10/1988 | Hall . | |
| 5,037,623 | * 8/1991 | Schneider et al. | 422/292 |
| 5,209,909 | * 5/1993 | Siegel et al. | 422/292 |
| 5,267,646 | 12/1993 | Inoue et al. . | |
| 5,552,115 | * 9/1996 | Malchesky | 422/28 |
| 5,662,866 | * 9/1997 | Siegel et al. | 422/29 |
| 5,720,930 | * 2/1998 | Bean | 422/300 |
| 5,755,330 | 5/1998 | Siragusa et al. . | |
| 5,997,814 | * 12/1999 | Minerovic et al. | 422/29 |

FOREIGN PATENT DOCUMENTS

| | | |
|---|---|---|
| 92310420.2 | 11/1992 | (EP) . |
| WO 97/11723 | 9/1996 | (WO) . |
| WO 97/13470 | 9/1996 | (WO) . |

* cited by examiner

Primary Examiner—Robert J. Warden, Sr.
Assistant Examiner—Monzer R. Chorbaji

(57) ABSTRACT

An outer, first container portion (50) has a peripheral wall (52) which has an opening at a first end (56) and at a second end (60). A porous filter (58) covers the second end. An inner, second container portion (70) has a peripheral wall (72) with a region which is formed from a first material which is impermeable to the powdered reagents but is permeable to water and to solutions containing dissolved reagents. The first and second container portions are configured such that the second container portion peripheral wall abuts and is connected to the first end of the outer first container portion. The first and second container portions define a first powdered reagent receiving chamber in the first container portion for receiving a first reagent and a second powdered reagent receiving chamber in the second container portion for receiving a second reagent. The porous filter is impermeable to the first reagent but permeable to water and to solutions containing dissolved reagents.

40 Claims, 12 Drawing Sheets

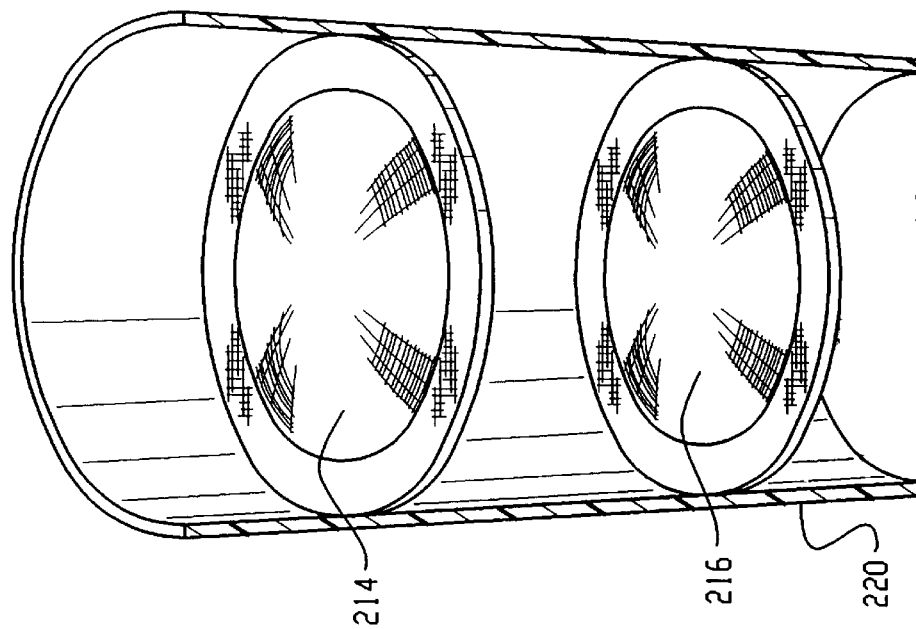
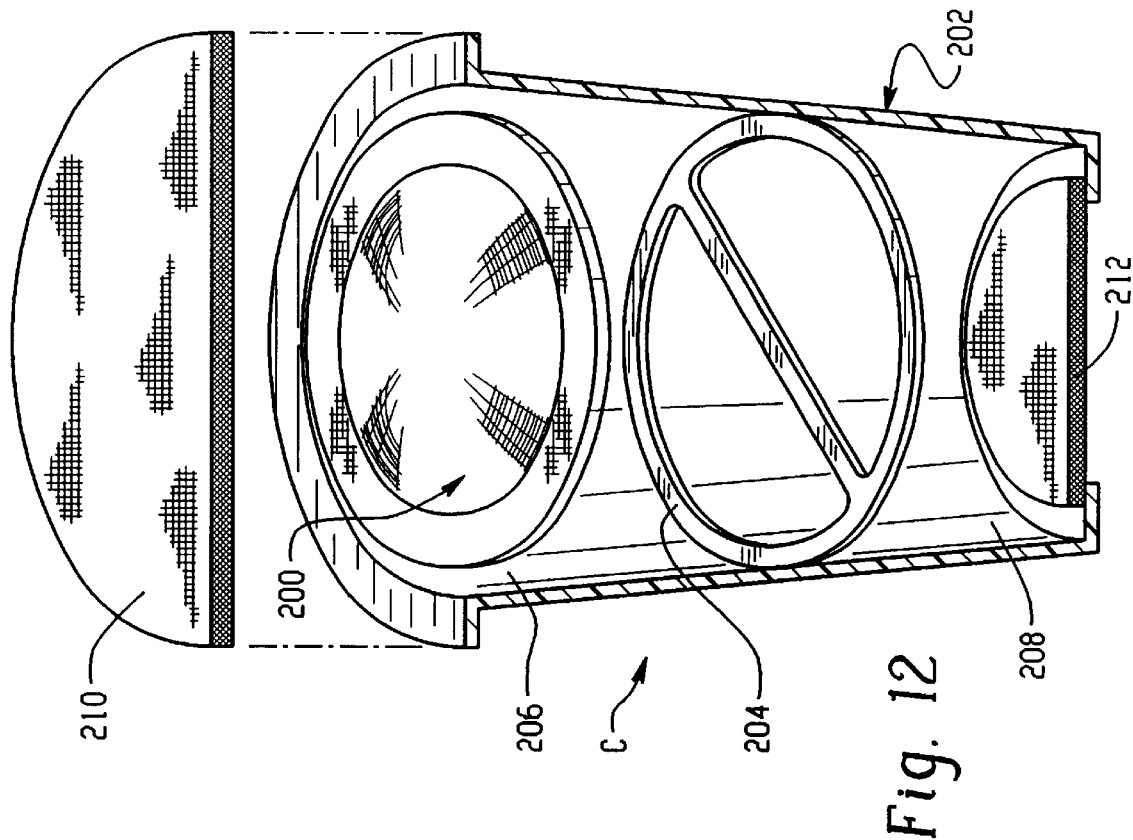

ANTIMICROBIAL COMPOSITION DELIVERY SYSTEM WITH AN INTEGRATED FILLER

This application claims the benefit of the Dec. 23, 1997, filing date of Provisional Application Ser. No. 60/070,930.

BACKGROUND OF THE INVENTION

The present invention relates to the decontamination arts. It finds particular application in conjunction with powdered reagents which are reacted in situ to form a liquid sterilant solution for sterilizing or disinfecting medical instruments and equipment and will be described with particular reference thereto. It should be appreciated, however, that the invention is also applicable to a wide variety of technologies in which at least two components or reagents are kept separate until time of use and then combined through dissolution in a common solvent.

Disinfection connotes the absence of pathogenic life forms. Sterilization connotes the absence of all life forms, whether pathogenic or not. The term decontamination is used herein to connote sterilization, disinfection or other antimicrobial treatments.

Heretofore, medical equipment and instruments have often been decontaminated in a steam autoclave. Autoclaves kill life forms with a combination of high temperature and pressure. However, steam autoclaves have several drawbacks. The high temperature pressure vessels tend to be bulky and heavy. The high temperature and pressure tends to curtail the useful life of endoscopes, rubber and plastic devices, lenses, and portions of devices made of polymeric materials and the like. Moreover, a typical autoclave decontaminating and cool down cycle is sufficiently long that multiple sets of the medical instruments are commonly required.

Instruments which cannot withstand the pressure or temperature of the oven autoclave are often decontaminated with ethylene oxide gas, particularly in larger medical facilities or hospitals. However, the ethylene oxide decontamination technique also has several drawbacks. First, the ethylene oxide decontamination cycle tends to be even longer than the steam autoclave cycle. Another drawback is that ethylene oxide decontamination is sufficiently sophisticated that trained technicians are commonly required, making it unsuitable for physician and dental offices and for other smaller medical facilities. Moreover, some medical equipment can not be decontaminated with ethylene oxide gas.

Liquid decontamination systems have also been utilized for equipment which could not withstand the high temperatures of steam decontamination. Commonly, a technician mixes a liquid disinfectant composition immediately prior to use and manually immerses the items to be decontaminated. The high degree of manual labor introduces numerous uncontrolled and unreported variables into the process. There are quality assurance problems with the weakening of the decontaminant chemicals due to aging on the shelf, and technician errors in the mixing of decontaminant, control of immersion times, rinsing of residue, exposure to the ambient atmosphere after the rinsing step, and the like. On occasion, powdered reagents are carried away from the mixing region and deposited in undesired locations before they dissolve or react. When systems are used for decontaminating medical instruments, undissolved reagent particles remaining on the medical instruments after a decontamination cycle are considered undesirable.

U.S. Pat. No. 5,662,866 to Siegel, et al. discloses a two-compartment cup for powdered sterilant reagent components. An outer cup holds a first reagent while an inner cup, disposed within the outer cup, holds a second reagent. Peripheral walls of inner and outer cups are affixed together at their open ends at flanges. A permeable sheet is affixed to the inner cup portion flange for ventedly sealing both cups. The outer cup is closed at its base by a first detachable base and the inner cup similarly closed by a second detachable base. In use, the two bases are opened to allow mixing of the two reagents. The two-compartment cup ensures sterilization or disinfection with a reproducible, pre-measured dose of reagents, while also facilitating handling and shipping of the reagents.

The present invention provides for a new and improved two compartment package which does not require detachment of first and second compartment bases and which is ideal for storing powdered reagents which are retained separately until time of use and are released in solution when a solvent is passed through both compartments.

SUMMARY OF THE INVENTION

In accordance with one aspect of the present invention, a multi-compartment package for holding powdered reagents which interact with water to form an anti-microbial solution is provided. The package includes:

a) an outer, first container portion including a first peripheral wall which defines a base extending to a continuous side with an opening at an end, and b) an inner, second container portion including a second peripheral wall which defines a base extending to a continuous side with an opening at an end.

The first and second container portions are configured such that the second peripheral wall abuts and is connected to the outer first container portion adjacent the end of the first peripheral wall. A top cover covers the openings in the first and second container portions. The first and second peripheral walls are configured such that a first powdered reagent receiving chamber is defined in the first container portion for receiving a first reagent and a second powdered reagent receiving chamber is defined in the second container portion for receiving a second reagent. The first peripheral wall includes a region which is formed from a first material which is impermeable to the first reagent but is permeable to water and to solutions containing dissolved reagents. The second peripheral wall includes a region which is formed from a second material which is impermeable to the first and second reagents but is permeable to water and to solutions containing dissolved reagents.

In accordance with another aspect of the present invention, a flow-through reagent cartridge for holding powdered reagents which interact with a solvent to form an anti-microbial solution is provided. The cartridge includes:

a) a first reagent receiving compartment which receives a first particulate reagent and is sealed against escape of the first particulate reagent received therein and which selectively releases dissolved reagent and b) a second reagent receiving compartment which receives and is sealed against escape of a second particulate reagent received therein and which selectively releases dissolved reagent.

The cartridge is configured for selectively holding the first and second powdered reagents separately within the cartridge and for permitting dissolved first and second reagents to pass out of the cartridge.

In accordance with yet another aspect of the present invention, a multi compartment package for separately holding a first reagent and a second reagent which react in water to form an anti-microbial solution is provided. The package includes:

a) a first container which holds the first reagent, the first container defining an inlet region through which water is received and an outlet region through which water and dissolved first reagent are discharged, b) a second container which holds the second reagent, the second container defining an inlet region through which water is received and an outlet region through which water and at least dissolved second reagent are discharged, and c) a porous medium which permits the passage of water, the anti-microbial solution, and water with dissolved first and second reagents, and which blocks the passage of undissolved first and second reagents, the porous medium being disposed at the first container inlet region and at the second container outlet region.

In accordance with a still further aspect of the present invention a method is provided. The method includesmetering a preselected volume of a first powdered reagent into a first container, the first container including a region of a first porous material which is impermeable to the first reagent but is permeable to water and to aqueous solutions containing dissolved reagents. The method further includes inserting a second container into the first container, the second container including a region of a second porous material which is impermeable to the first reagent and to a second reagent but is permeable to water and to solutions containing dissolved reagents.

The method also includes connecting the second container to the first container, metering a preselected volume of the second powdered reagent into the second container, and closing the first and second containers.

In accordance with a still further aspect of the present invention, a decontamination system is provided. The system includes a powdered reagent container receiving well. A first fluid flow path is defined between a water receiving inlet and the reagent container receiving well to bring water from the inlet to the well to mix with powdered reagents and form a decontaminant solution. A second fluid flow path is defined for the decontaminant solution from the reagent container receiving well to a decontamination region for receiving items to be decontaminated. A fluid circulator selectively circulates fluid through the first and second fluid flow paths and among the inlet, the decontamination region, and the reagent container receiving well. A multi-chamber powdered decontamination reagent holding container is inserted into the well, the container including:

a) an outer, first container portion including a first peripheral wall which defines a first end with an inlet opening and a second end with an outlet opening, the outlet opening being closed with a material which is impermeable to undissolved reagents held in the container and is freely permeable to aqueous solutions, b) an inner, second container portion including a second peripheral wall which defines a first end with an inlet opening and a second end with an outlet opening the first and second container portions being nested, and c) a top cover covering the first and second container portion inlets.

In accordance with another aspect of the present invention, a method of decontamination is provided. The method comprises inserting a multi-chamber powdered decontamination reagent holding container into a powdered reagent container receiving well. The container includes first and second container portions. The method includes supplying water to the well to mix with powdered reagents in the container and form a decontaminant solution, and transporting the decontaminant solution to a decontamination region for receiving items to be decontaminated.

One advantage of the present invention is that it facilitates materials handling.

Another advantage of the present invention is that it simplifies filling and sealing of two reagents in separate compartments.

Another advantage of the present invention is that it promotes thorough mixing of the reagents and complete dissolution of the reagents.

Another advantage of the present invention is that undissolved particles of reagent remain trapped within the cartridge until dissolved.

Another advantage of the present invention is that it enables release of dissolved reagents from the package without first opening the package.

Another advantage of the present invention is that it permits introduction of reagents at different rates.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 12 is an expanded view of yet another alternate embodiment of the package of FIG. 3; and, FIG. 13 is an expanded view of yet another alternate embodiment of the package of FIG. 3.

DETAILED DESCRIPTION OF THE PREFERRED EMBODIMENTS

Figure 1:
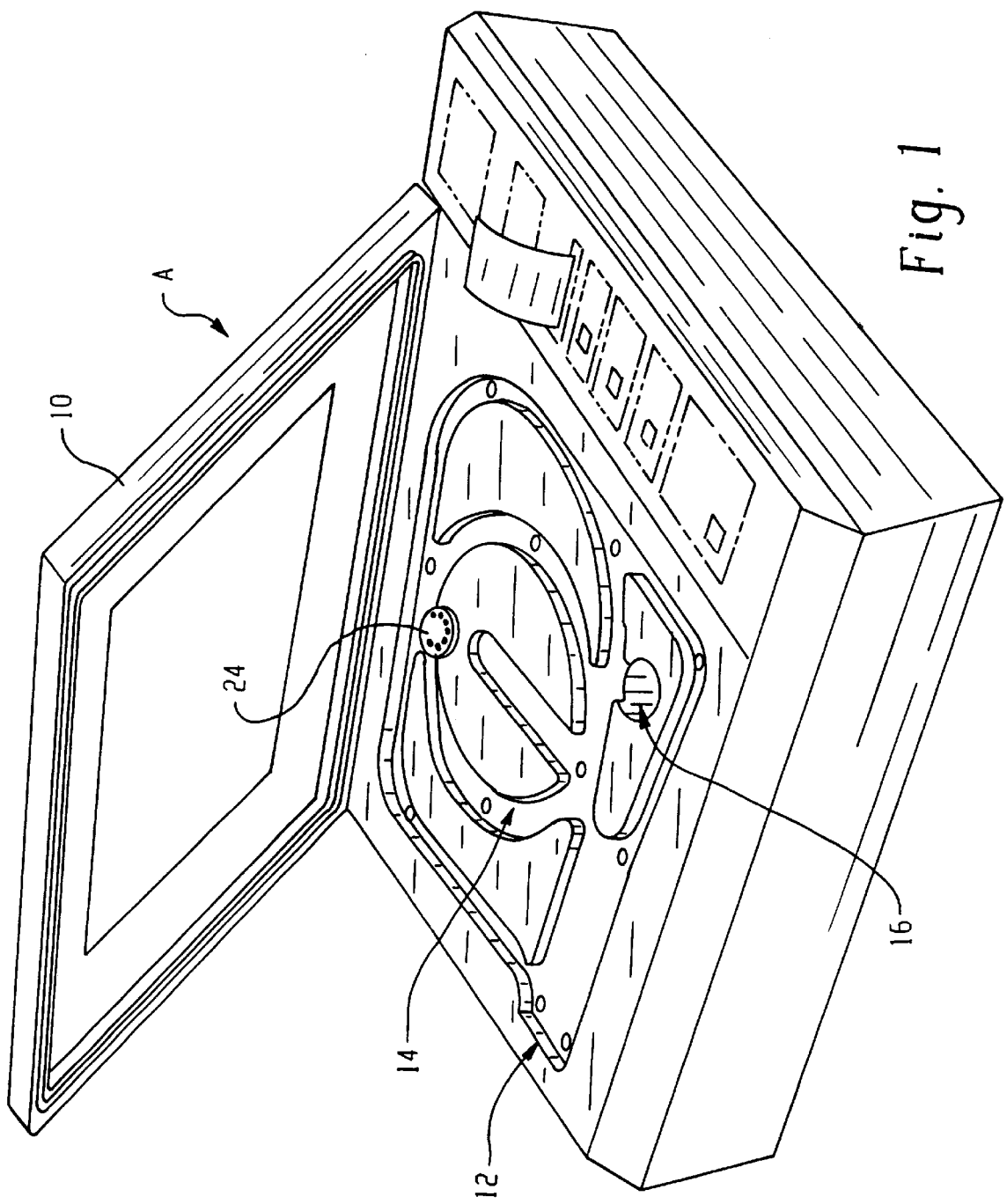
FIG. 1 is an exterior view of a decontamination unit according to the present invention.
Figure 2:
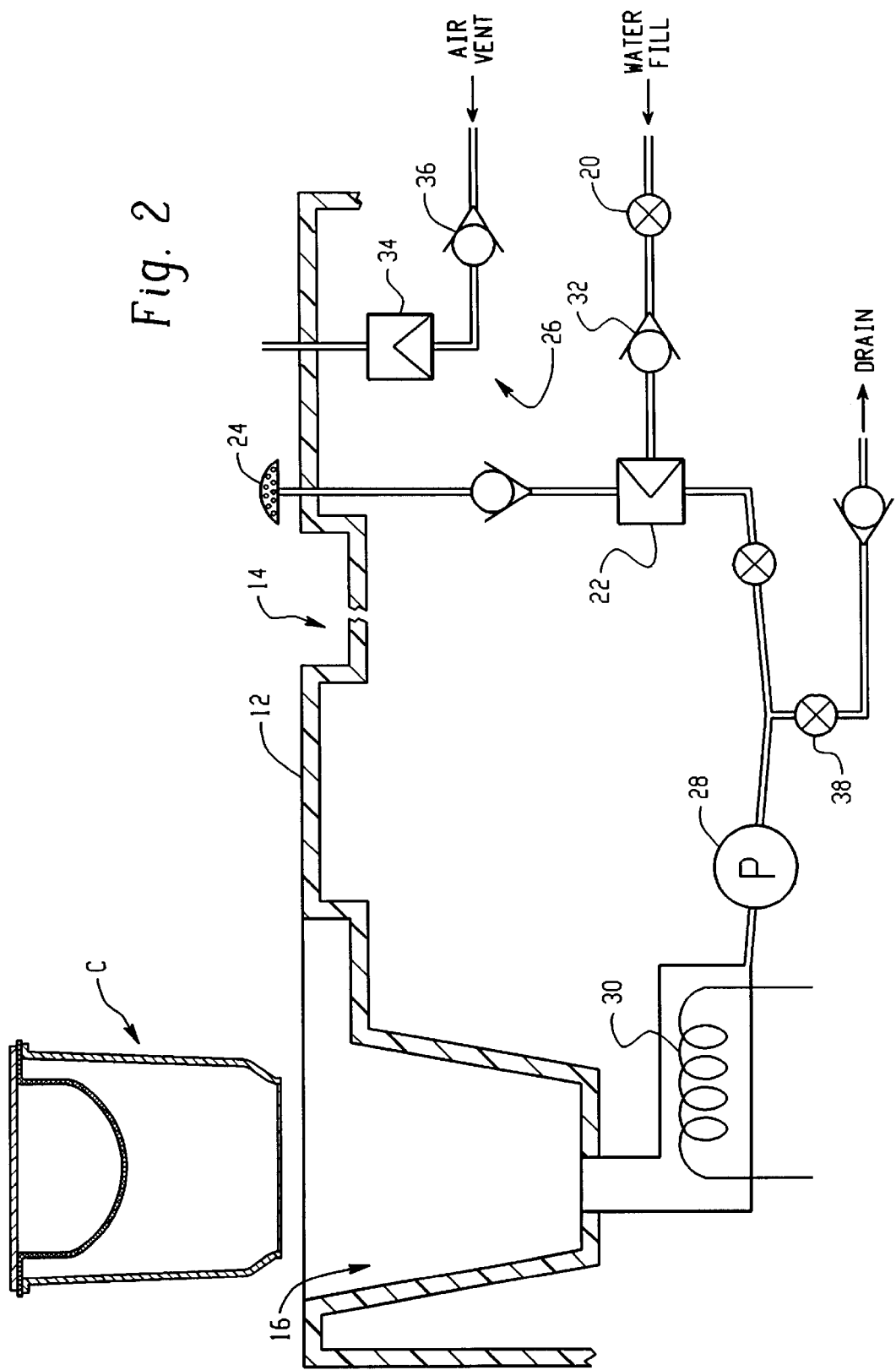
FIG. 2 is a plumbing diagram of the decontamination unit of FIG. 1 including a cross-sectional view of a reagent cartridge receiving well and one embodiment of a two-compartment reagent package according to the present invention.

With reference to FIGS. 1 and 2, a microbial decontamination apparatus A is configured to sit on a counter top or other convenient work surface. A door or lid 10 is manually openable to provide access to a tray 12 which defines a receiving region 14 for receiving items to be microbially decontaminated. In the illustrated embodiment, the tray 12 is configured to receive endoscopes or other long, coilable items. Other trays with item receiving regions of different configurations for receiving the items themselves or item holding containers are also contemplated. A well 16 receives a unit dose of reagents for forming a sterilant, disinfectant, other microbial decontaminating solution, detergent or cleaning solution, or the like.

With particular reference to FIG. 2, a reagent containing package or cartridge C is inserted into the well 16. Once the items are loaded into the tray and the reagent carrying package C is inserted into the well 16, the lid 10 is closed and latched. A fill valve 20 passes water through a microbe removing HEPTA filter 22 in flow paths of a fluid circulating system. The microbe removing filter 22 provides a source of sterile water by passing water and blocking the passage of all particles the size of microbes and larger. The incoming water which has been sterilized by the filter 22 passes through a spray or distribution nozzle 24 and fills the item receiving region 14 in the tray 12. As additional water is received, it flows into the well 16 dissolving powdered, crystalline, encapsulated, or other non-flowing reagents in the package C, forming an anti-microbial solution. Filling is continued until all air is forced through an air system 26 and an entire interior volume is filled with the sterile water. After the fill valve 20 is closed, a pump 28 circulates the fluid through a heater 30, the item receiving region 14 of the tray 12, and the well 16. The pump also forces the anti-microbial solution through the filter 22 to a check valve 32, thereby sterilizing the filter. Further, the pump forces the anti-microbial solution through another microbe filter 34 in the air system 26 to a check valve 36.

After the anti-microbial solution has been brought up to temperature and circulated over the items to be microbially decontaminated for a selected duration, a drain valve 38 is opened, allowing the solution to drain. Air is drawn through the microbe filter 34 such that sterile air replaces the fluid within the system. Thereafter, the drain valve is closed and the fill valve 20 opened again to fill the system with a sterile rinse fluid. It will be noted, that because the pump 28 circulated the anti-microbial solution over all surfaces of the flow paths including all surfaces leading from the sterile rinse source, microbe removing filter 22, the rinse cannot bring microbial contaminants into the item receiving region 14.

Figure 3:
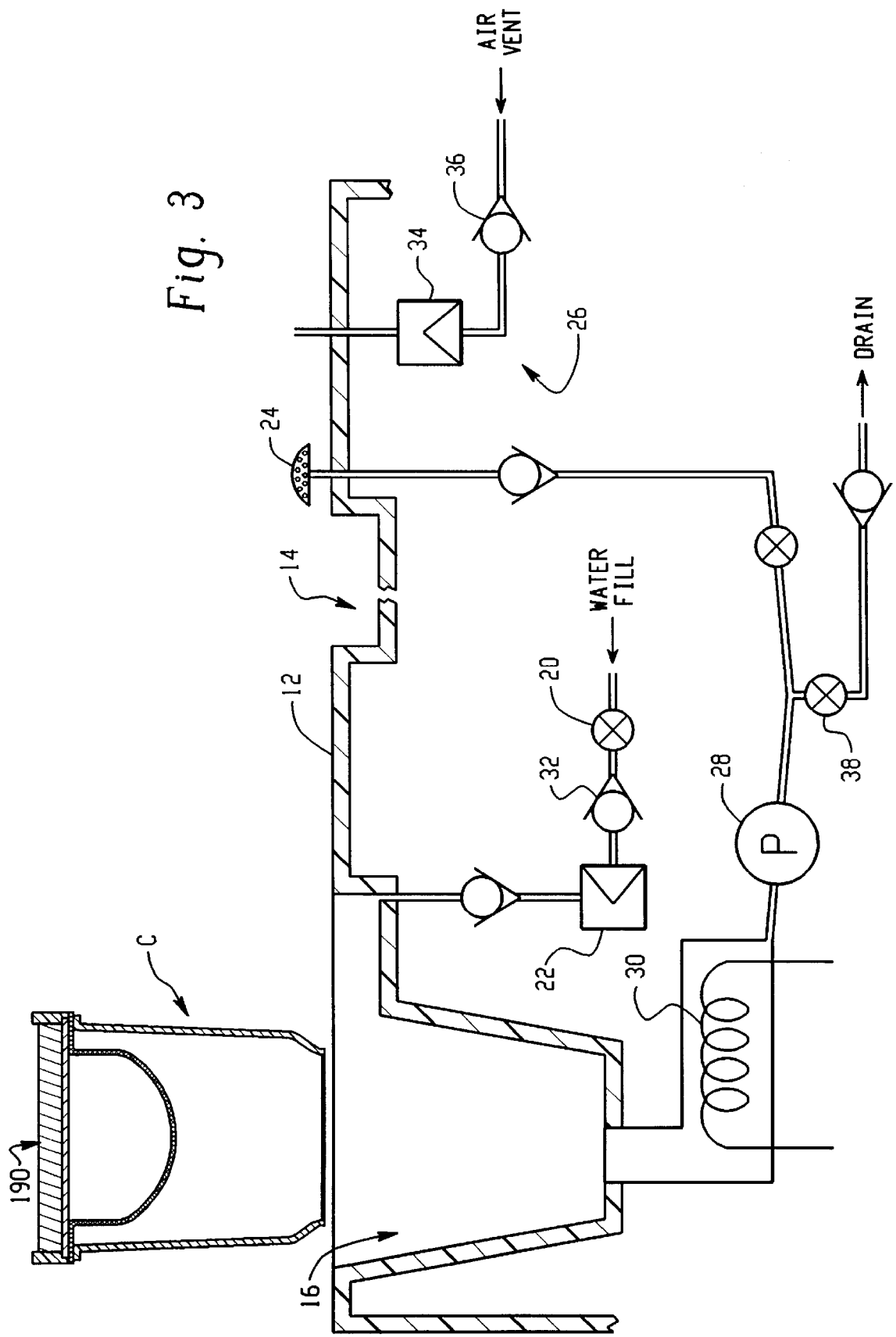
FIG. 3 is a plumbing diagram of a second embodiment of the decontamination unit of FIG. 1 according to the present invention.

With reference to FIG. 3, an alternative embodiment of the decontamination apparatus A is shown. In this embodiment, incoming water passes from the microbe removing filter 22 to the well 16, without first passing through the receiving region 14. Optionally, the reagent containing package C includes the microbe removing filter 22, as will be discussed later.

Figure 4:
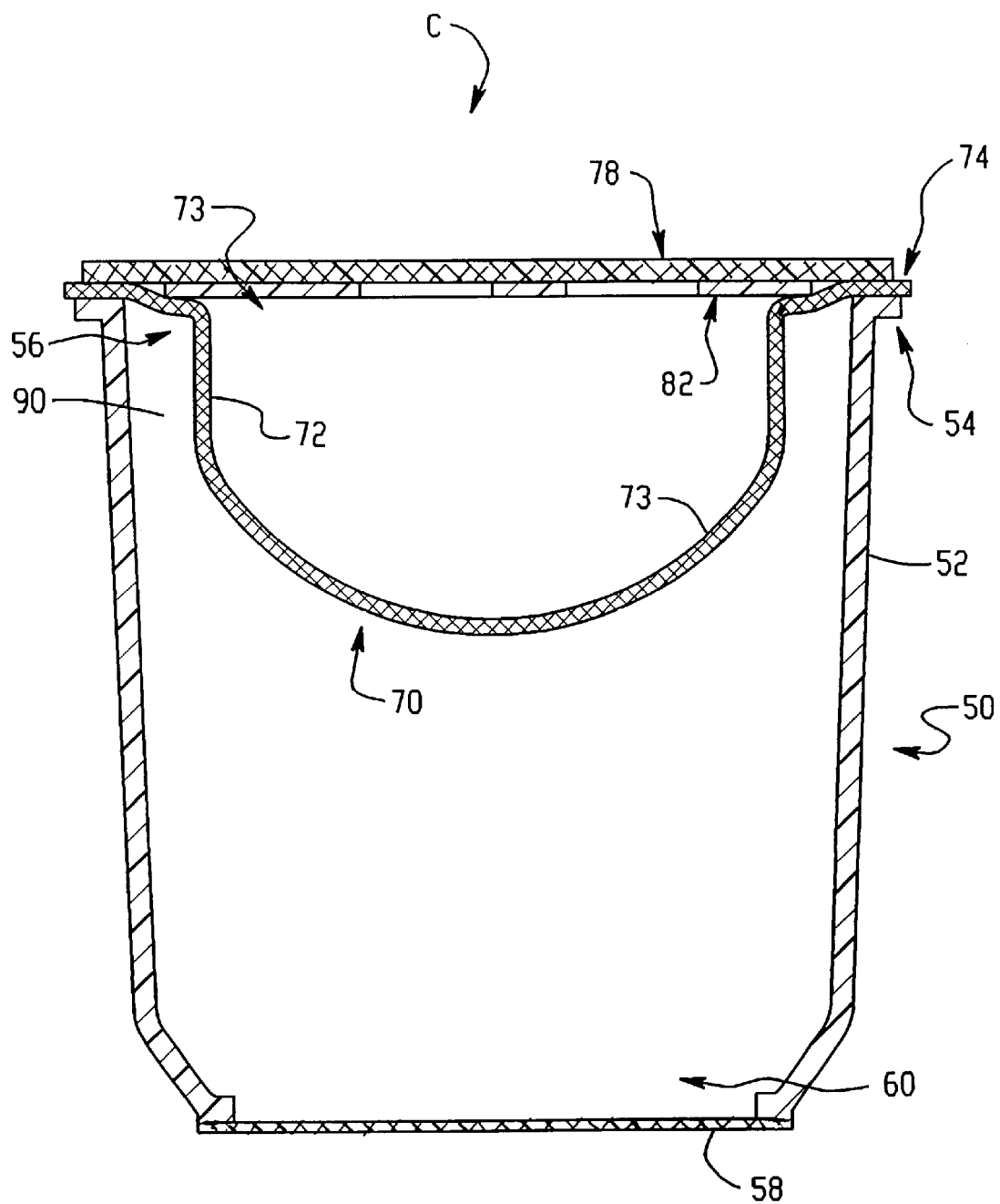
FIG. 4 is a side sectional view of a first embodiment of the two compartment package in accordance with the present invention.
Figure 5:
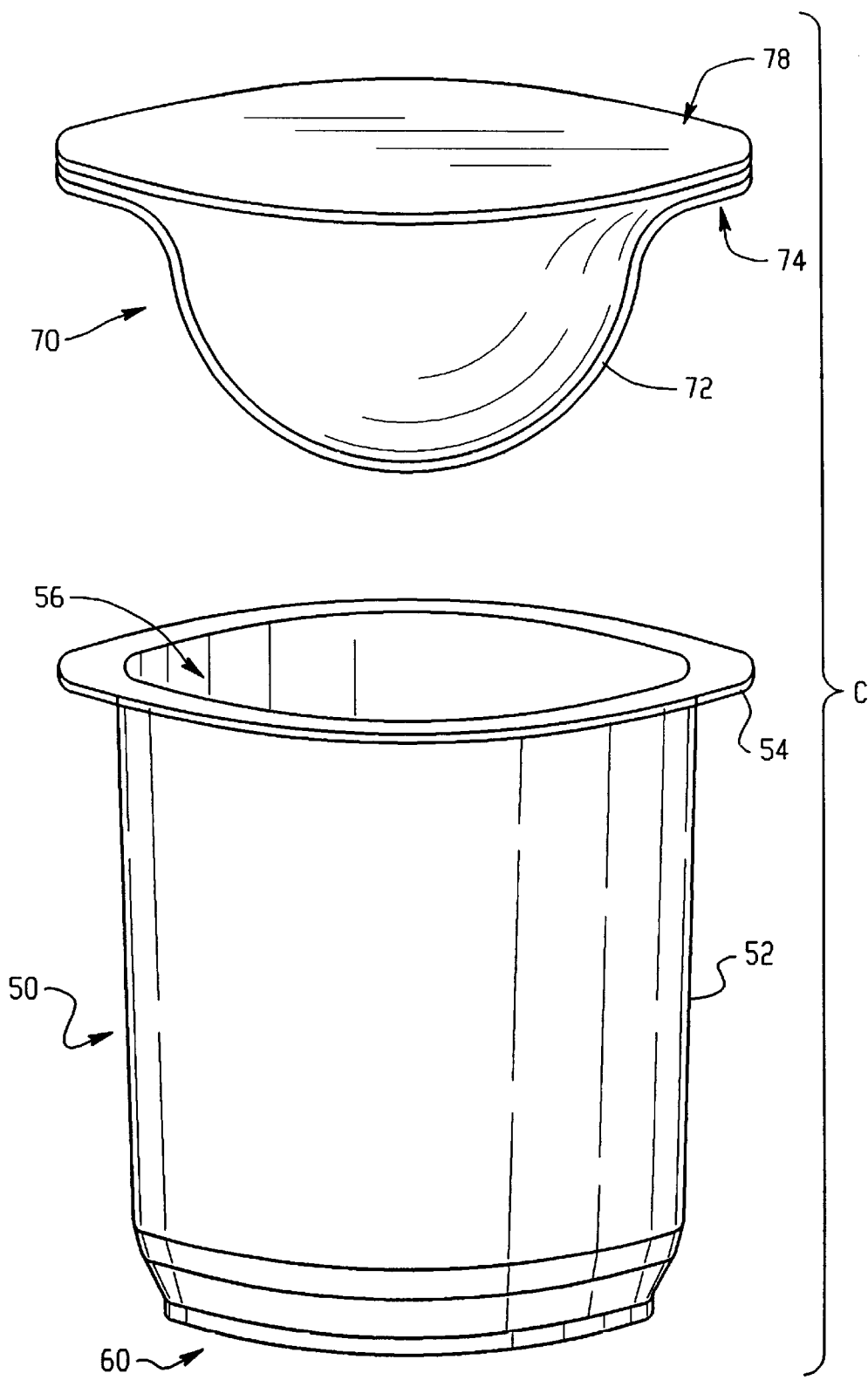
FIG. 5 is an expanded perspective view of the two-compartment package of FIG. 4.

With reference to FIGS. 4 and 5, a first embodiment of the package C includes a first, or outer container portion 50. The outer container 50 is constructed of a light weight, rigid polymeric material. The outer container 50 includes a cylindrical peripheral wall 52 that has a flange 54 at a first, open end 56 thereof. A fluid-permeable base, or porous filter 58 covers a second, opposite, or lower end 60 of the peripheral wall 52. The porous filter 58 is ultrasonically welded or otherwise adhered to the peripheral wall 52 covering the lower end 60 in the outer container. The outer container is then filled with reagent components, such as sodium perborate, corrosion inhibitors, pH buffers, detergents and wetting agents. The filter 58 is preferably formed from a material that is impermeable to the dry reagents that are contained within the first container portion, yet is permeable to water with dissolved reagents.

A second, or inner container portion 70 is received in the first container portion 50. The second container portion includes a thermally molded, peripheral wall 72 which defines a generally hemispherical cup with a top opening 73, and an integrally molded flange 74. Alternatively, the second container peripheral wall is cone or cylindrically shaped. The inner container 70 is filled with a second reagent component, preferably an acetyl donor such as acetylsalicylic acid.

The peripheral wall 72 of the second container portion 70 is formed from a filter material that is impermeable to the dry reagents contained within the first and second container portions, yet is permeable to water and to the dissolved reagents. Suitable filter materials include polypropylene, polyethylene, nylon, rayon, rigid porous media, such as POREX™ expanded plastic, or other porous plastic, fabric, felt, mesh, and analogous materials. Alternatively the peripheral wall 72 includes only a limited region that is formed from a material which is impermeable to the powdered reagents but which is permeable to water and to the dissolved reagents.

A top cover 78 covers the top opening 73 of the second container portion. Any particles of reagent in the second container portion 70 that are not dissolved are therefore trapped within the second container portion. Preferably, the top cover is also formed from a similar filter material to that of the peripheral wall 72, or includes a porous region. Dissolved reagents pass through the layers of porous material and are transported to the items to be decontaminated.

With particular reference to FIG. 5, the inner container flange 74 is pressed against the top flange 54 for ultrasonic or heat welding. Preferably, an outer edge of the top cover 78 is sealed to the inner container flange 74 in the same welding operation. Analogously, the porous filter 58 is pressed against the flange on the outer container peripheral wall 52 around the opening 60 for ultrasonic or heat welding. Under heat or ultrasonic vibration, the plastic melts and flows into the fibers or the voids of other porous filter materials, forming a unitary seal. Alternatively, other methods of sealing such as gluing, fusion bonding, clamping with a clamping ring, or the like replace the heat or ultrasonic welding as a means of joining the various components.

Optionally, as shown in FIG. 4, a stiffener 82, such as an annular ring with a pair of x-shaped cross members, is positioned between the inner container 70 and the top cover 78 to ensure that the top cover lays flat. Preferably, the stiffener 82 is of smaller diameter than the weld rings 80 and is not incorporated into the weld. Rather, it is held in place by frictional or mechanical force.

The two compartment package C is alternatively constructed according to a variety of different embodiments which serve to keep the dry reagents in separate compartments during transportation and storage, yet allow the reagents to leave the package when dissolved in water, or other suitable solvent, that flows into the package.

Figure 6:
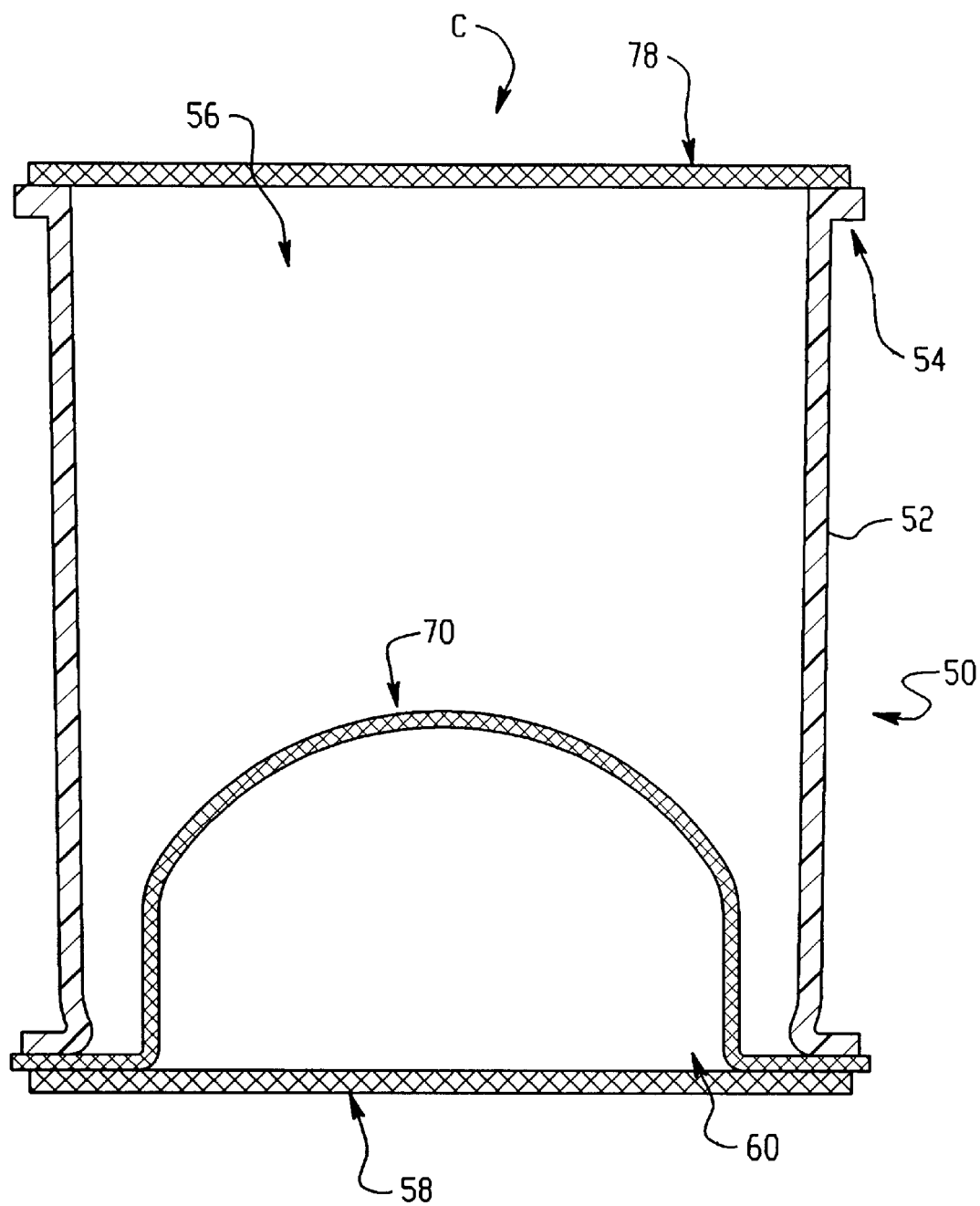
FIG. 6 is another alternate embodiment of the package of FIG. 3.

In the embodiment of FIG. 6, the inner container 70 is constructed in whole or part of a porous filter material. The inner container and filter layer 58 are welded or otherwise affixed to a lower end of the outer container peripheral wall 52 to cover the lower open end 60. One of the reagents such as acetylsalicylic acid or multiple components, is held in the inner container, and other reagents, such as a perborate, are held in the outer container 50. Upper filter layer 78 is welded across the top opening 56 of the outer container.

Figure 7:
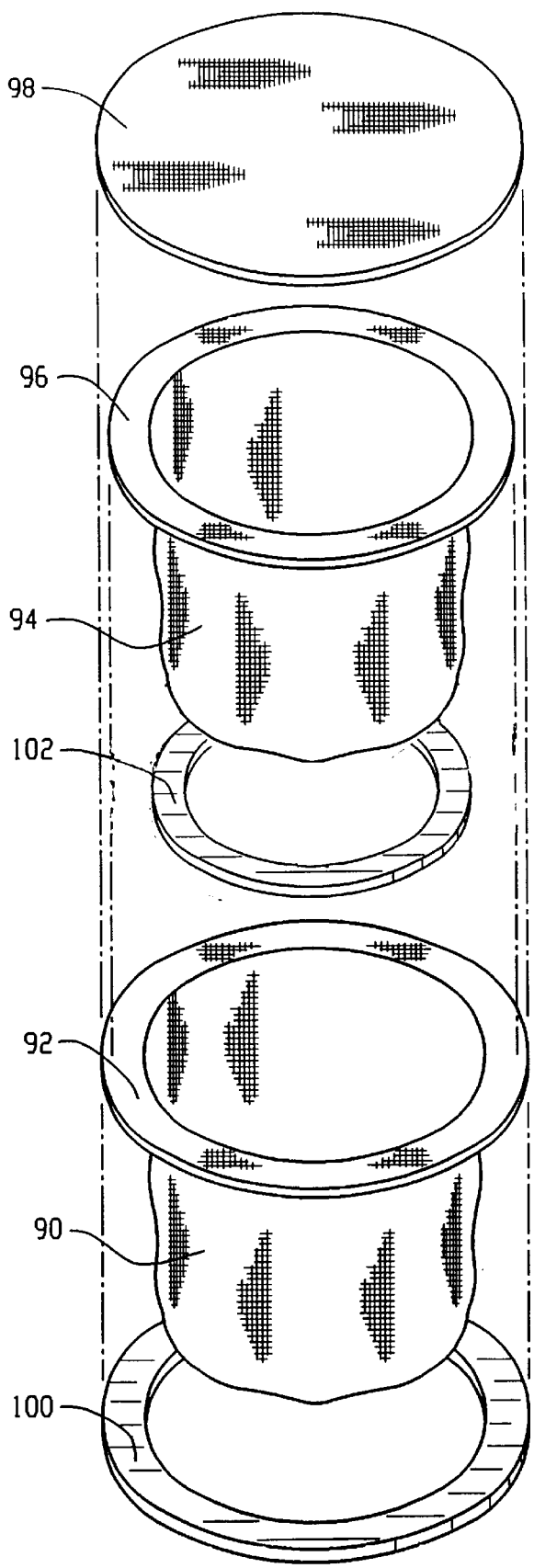
FIG. 7 is an expanded view of yet another alternate embodiment of the package of FIG. 3.

In the embodiment of FIG. 7, an outer container 90 is formed of a porous filter material. The outer container includes an upper flange 92. An inner container 94 is also formed of the filter material and, again, has an upper flange 96. The flanges of the inner and outer containers are pressed together along with a top filter layer 98 and are welded or otherwise adhered together to form sealed inner and outer container portions.

Optionally, for stiffness, an annular ring of rigid plastic 100 is welded or otherwise adhered to one or both of the flanges 92, 96. For additional stability, a retainer, such as a second annular ring 102 of rigid plastic is inserted into the bottom of the outer container to hold the bottom in a circular configuration. Alternatively, the inner and outer containers 90, 94 are formed, at least in part, from a rigid porous material, such as POREX™ expanded plastic, which retains its rigid structure when wet. Again, one or more of the powdered reagents is loaded into the inner container and the other into the outer container.

Figure 8:
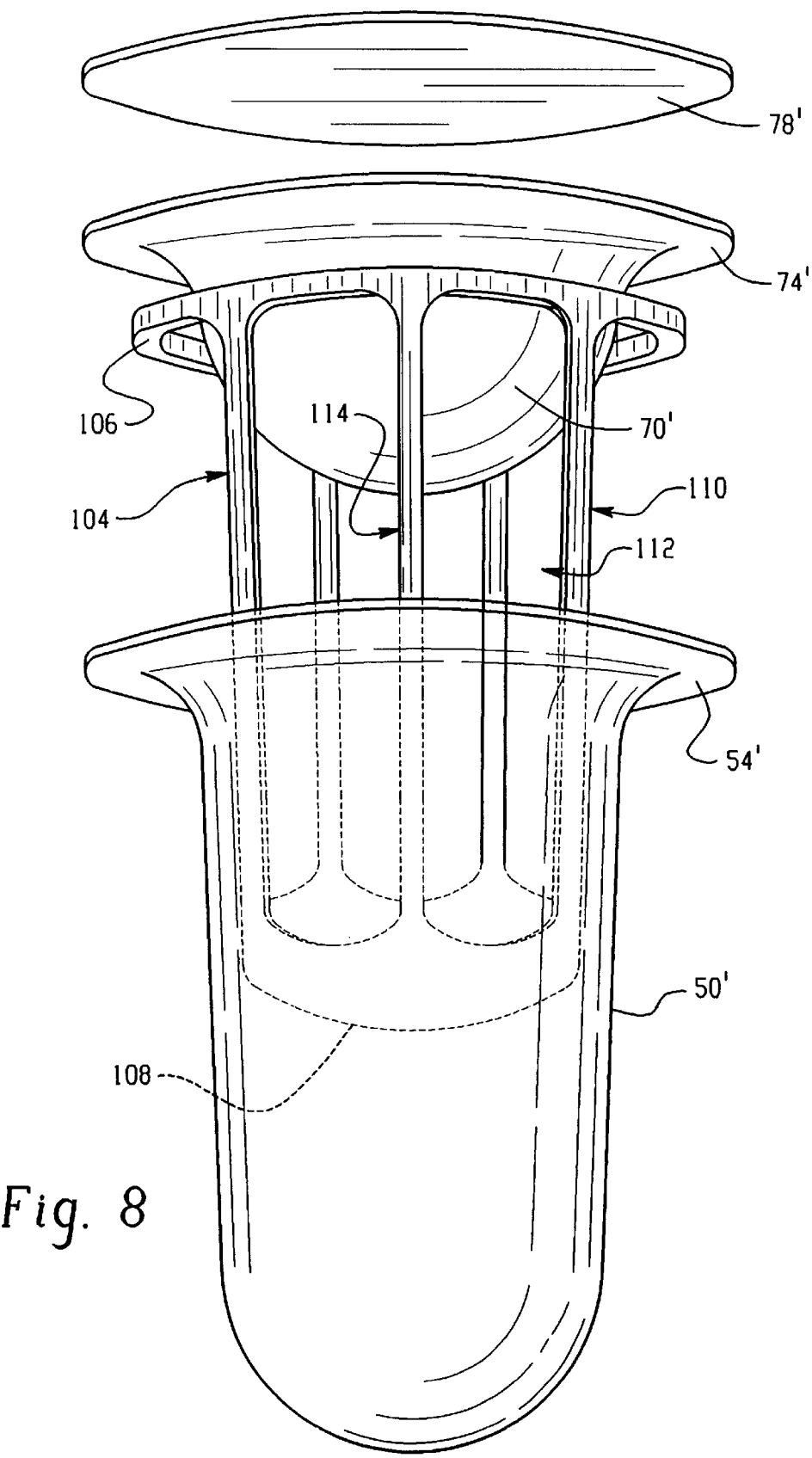
FIG. 8 is an expanded view of yet another alternate embodiment of the package of FIG. 3.

With reference to FIG. 8, an outer container 50' is formed of the filter material with an upper flange 54'. An inner container 70' is formed of the porous material with a flange 74'. A retainer, such as a frame member 104, constructed from a rigid material such as plastic, defines an upper shaping ring 106 and a bottom shaping ring or surface 108. The bottom shaping surface 108 is received into the outer filter material container 50' to force its base into a preselected shape. Sides 110 of the frame member 104 have large openings 112 separated by ribs 114 to assure adequate liquid flow paths. The upper ring 106 of the retainer 104 is held adjacent the flanges 74', 54' of the inner and outer containers when they are affixed together with an upper filter layer 78'. Again, the flanges may be welded, glued, fusion bonded, clamped with a clamping ring, or the like.

Figure 9:
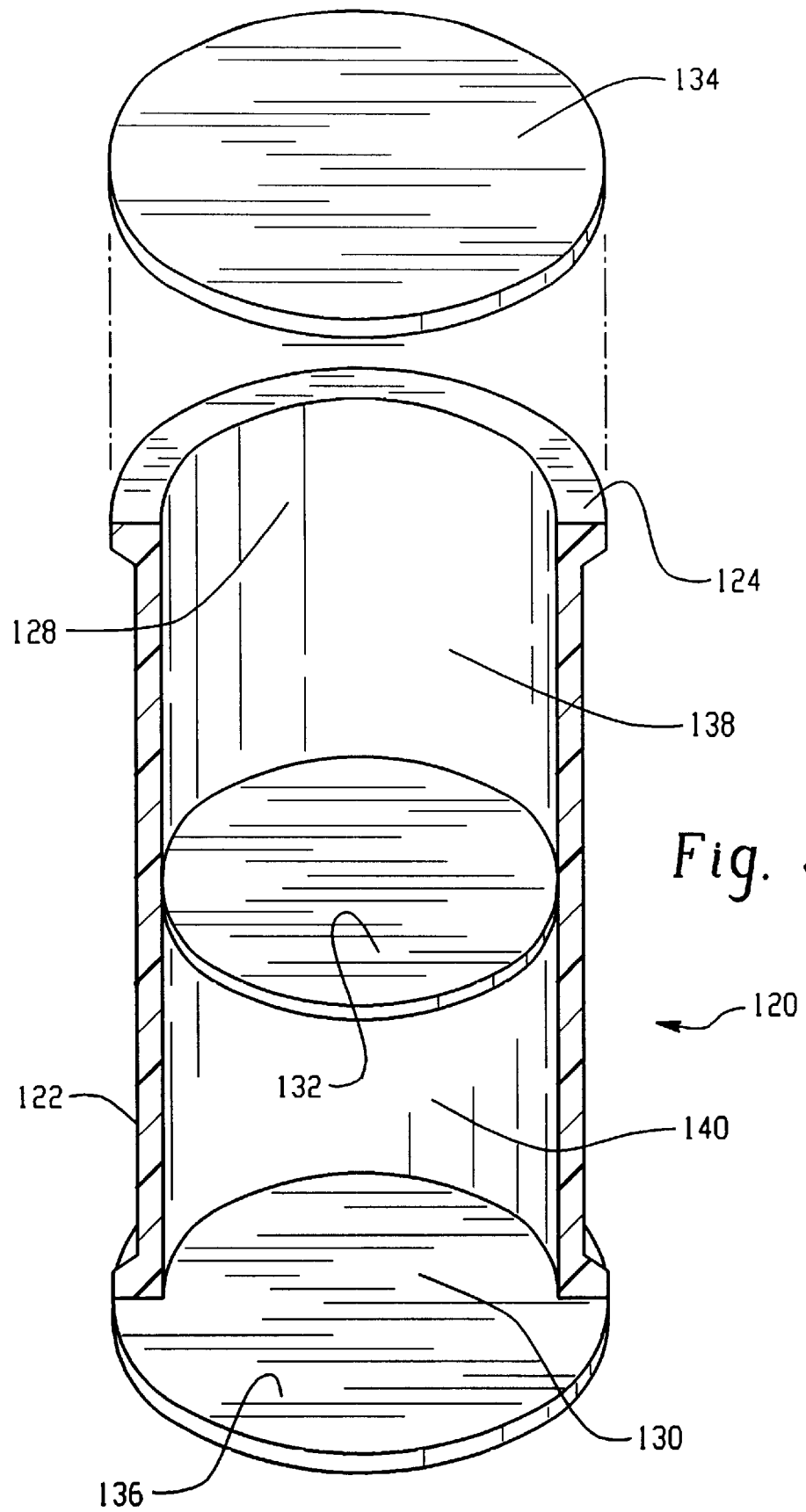
FIG. 9 is yet another alternate embodiment of the package of FIG. 3.

In the embodiment of FIG. 9, an outer container 120 includes a peripheral wall 122 constructed of a rigid plastic which defines the shape of a tube having upper and lower flanges 124 and 126, adjacent upper and lower openings 128 and 130, respectively. A horizontal dividing wall, or partition 132 separates the outer container 120 into two compartments. The dividing wall 132 is constructed of a porous plastic or filter material. A porous or rigid top cover 134 is sealed to the upper flange 124. A porous base 136 is sealed to the lower flange. One of the reagents is placed in a first compartment 138 defined on one side of the partition 132 and the other reagent is loaded into a second compartment 140 defined on the other side of the partition 132.

Figure 10:
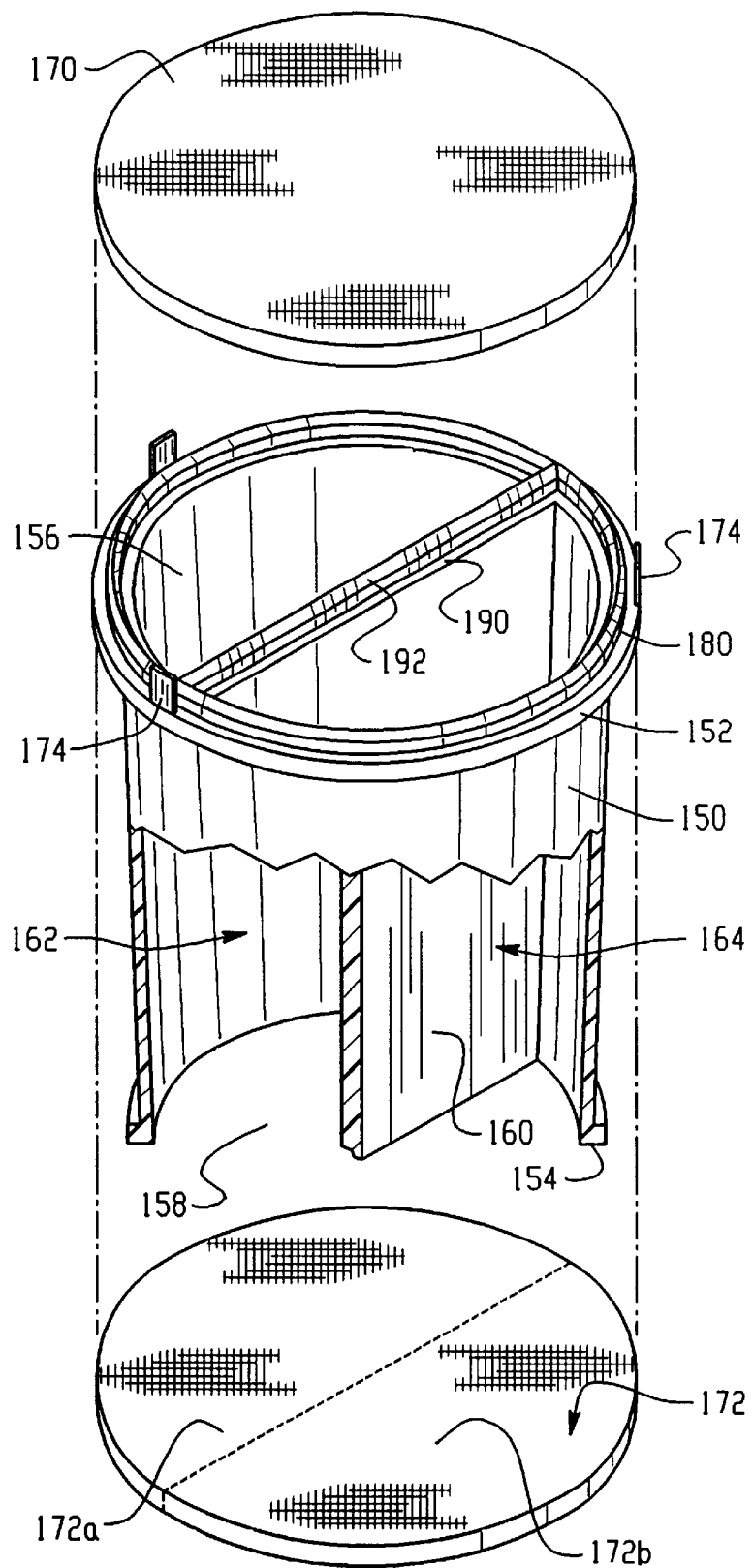
FIG. 10 is an expanded view of yet another alternate embodiment of the package of FIG. 3.

In the embodiment of FIG. 10 an outer container 150 of a rigid plastic material defines the shape of a tube having an upper flange 152 and a lower flange 154 adjacent upper and lower openings 156 and 158 in the container, respectively. A vertical dividing wall, or partition 160 separates the outer container 150 into two compartments. In the illustrated embodiment, the dividing wall 160 is constructed of rigid plastic, although porous plastics or filter material are also contemplated. One or more of the reagents is placed in a first compartment 162 defined on one side of the partition 160 and the other reagent(s) is loaded into a second compartment 164 defined on the other side of the partition 160. Other components, such as corrosion inhibitors, wetting agents, pH buffers, and the like are optionally loaded into one of the two compartments.

While the embodiments have been described with reference to two containers or compartments, alternately, one or more additional partitions are provided to divide the outer container into three or more compartments to receive the other components.

A top cover 170 formed from a layer of filter material or rigid plastic is welded or otherwise adhered to the upper flange 152 and the upper edge of the partition 160. Analogously, a base 172 formed from a layer of filter material is welded or otherwise adhered to the lower flange 154 and the bottom surface of the partition 160.

Alternatively, the base comprises two portions 172a and 172b which serve as a base for the first and second compartments, 162,164, respectively. The material of each of the portions is selected according to the particle size of the reagent to be loaded into the compartment, or according to a desired rate of solubilization of the reagent, as will be discussed later.

Preferably, the upper flange 152 of the outer container 150 of this, or any of the other embodiments includes a plurality of positioning tabs 174. The positioning tabs 174 are located radially outward beyond the top cover 170 and the weld. The tabs 174 extend upward a sufficient distance to engage a structure on the lid 10 of the decontamination apparatus A, or other internal lid, which presses against the tabs when the lid is closed at the commencement of a cycle. The tabs are spaced and sufficiently long that a fluid flow between the lid structure 10 and the cartridge C is assured.

Figure 11:
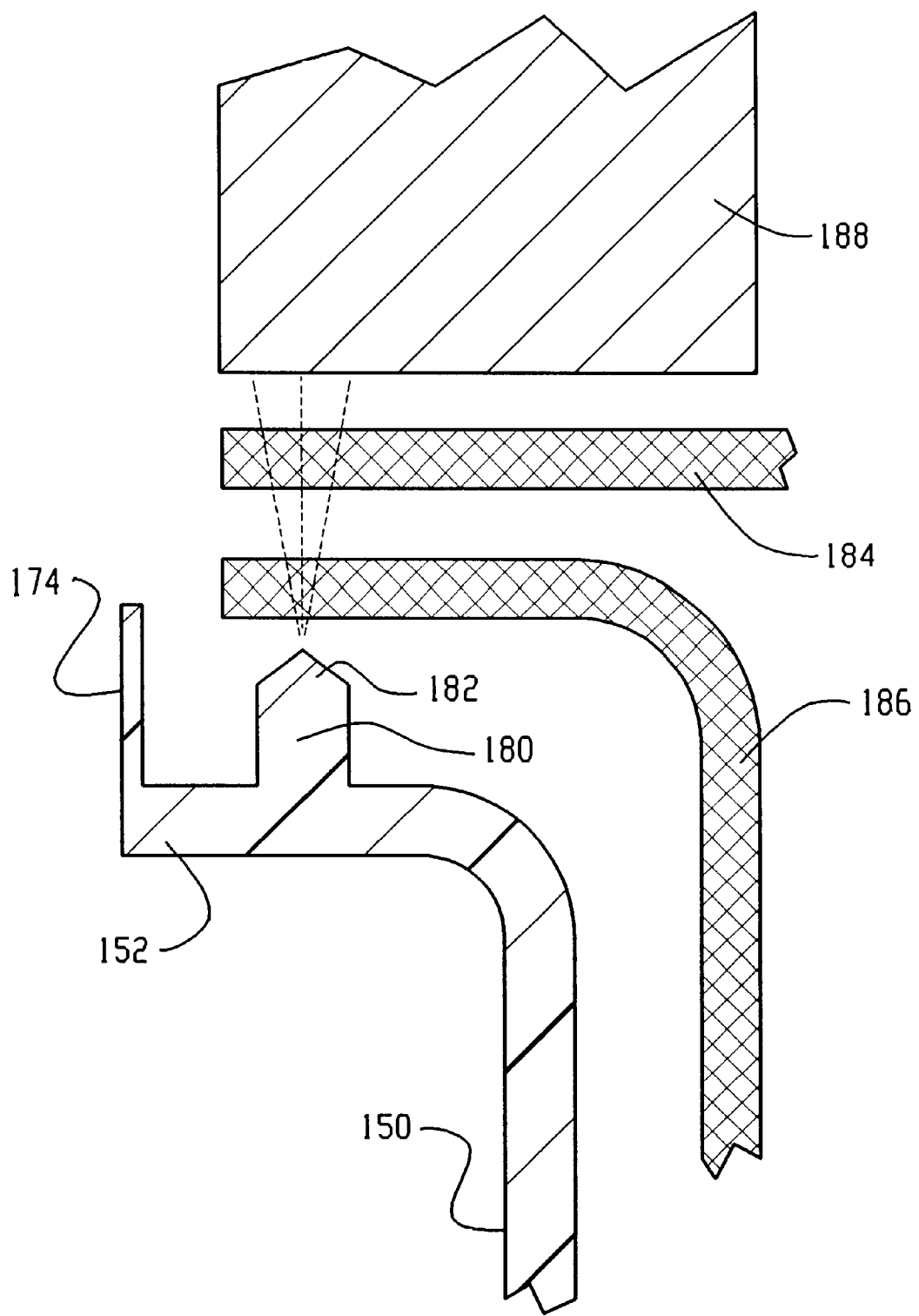
FIG. 11 is a detailed illustration of a preferred weld joint configuration.

With continued reference to FIG. 10 and reference also to FIG. 11, the upper flange 152 of the outer container 150 or of any of the other embodiments with a rigid outer container or a rigid annular ring includes an upward projecting energy director 180. The energy director 180 includes an upward projecting annular rib 182 extending around the flange 152. The rib is relatively narrow with a narrowing upper edge. A top cover 184 and, where present, a flange 186 of an inner container (such as for the embodiments of FIGS. 4, 5, or 7) are pressed against the energy director 180. The flange 186, and optionally the top cover 184, are formed from a porous filter material. A welding horn 188 presses the filter layers against the energy director with a significant force and concurrently applies ultrasonic vibrations and optionally heat. The ultrasonic vibrations are preferentially attracted to the raised energy director. The combination of pressure, heat, and vibration causes the energy director to fluidize, flowing into and through the filter material 186 to the top cover 184, forming a tight, unitary seal.

When the two compartments are formed by a vertical barrier, or dividing wall, as shown in FIG. 10, a top 190 of the barrier 160 also includes an energy director 192 for sealing the top cover to the barrier. Analogously, similar energy directors on the lower flange 154 of the outer container and on a lower end of the barrier assist in welding on the porous base 172.

The flow-through design of the package allows for integration of filters with absolute ratings into the package which allows for segregation of the components and prevents sifting of particles due to particle size exclusion. The preferred design uses polypropylene, polyethylene, blended polyolefin non-woven material, or a porous media for one or more of the filters. The filter optimizes solubility by increasing flow through the package and prevents any material from escaping the filter package without being solubilized. The flow-through filter design allows for complete segregation of the materials during shipment and storage. It further provides for complete retention of the particles and the chemistry while the delivery system is being flooded. Further, the design allows the constituents to be released and reacted together without opening, or puncturing, the cartridge. The filter layer further provides a gross filter for any particles that might be washed off the instruments being decontaminated in the tray 12.

The inner container can take various shapes including truncated cones, cones, and the like. It can be constructed totally of filter material or only partially of a filter material. For example, the inner compartment can have peripheral walls and a flange of solid plastic with the filter material supported across the bottom of the inner container. A lower flange on the inner container facilitates welding or bonding and crossing ribs can provide structural support to the filter layer at the bottom of the inner container. Optionally, one or more of the filter layers can be replaced with an openable or severable barrier. For example, the bottom of the inner container can be constructed of a film which breaks when water is introduced into the system. The film may be constructed of a water-soluble material, or of a material which becomes sufficiently weakened in the presence of the water or water and powdered reagents that it ruptures under the pressure applied by the pump 28. As another alternative, the bottom of the inner container may open in response to pressure applied to the peripheral walls of the outer container. Other release mechanisms for releasing the bottom of the inner container are also contemplated.

Alternately, the bottom of the inner container can be a filter material, and the bottom opening of the outer container can be a releasable member. When the bottom of the outer container is releasable, it is preferred that the most soluble reagents be positioned in the outer container and the less soluble reagents positioned in the inner container.

In another embodiment, the top cover is impermeable to water and may be integrally formed with the outer container. Water enters the cartridge through an opening which is pierced in the top cover at the commencement of the decontamination cycle.

In yet another embodiment shown in FIG. 12, one of the compartments is defined by a filter bag 200, formed from a porous material, which encloses one of the dry reagents and which is impermeable to dry reagents yet allows water and dissolved reagents to pass freely through the cartridge C. Preferably the bag is retained in the cartridge such that water flowing through the cartridge must pass through the filter bag. optionally, the bag is supported within the outer compartment 202 on an open support 204, such as a mesh screen. The outer compartment is covered at inlet and outlet ends 206 and 208, respectively, by sheets of porous material 210 and 212.

Alternatively, as shown in FIG. 13, each of the reagent compartments is defined by a filter bag, 214 and 216, respectively, disposed within an outer container 218. Preferably, these are retained within an outer container 220 such that water flowing through the container passes through both compartments.

The choice of filter material depends on the particle size of the reagents. For reagents having a particle size of about 50 microns, a non-woven polypropylene web or felt keeps the dry reagents from penetrating the material, while allowing the water and dissolved reagents to pass freely through the cartridge. When the material is a polypropylene web, the top cover is readily sealed to the second container portion by ultrasonically welding or other heat sealing the flange of the second container portion to the top cover.

Moreover, the choice of filter material affects the rate of solubilization of the reagents. By selecting the dimensions of the pores appropriately, turbulence is created within and adjacent the pores, assisting in solubilization of the reagents.

Particularly when the construction of the cartridge permits separate water flow through each of the two compartments, as in the embodiment of FIG. 10, the filter material of one of the compartments is optionally selected to delay the rate of introduction of the reagent contained within that compartment to the flow of water passing through the cartridge. By limiting the pore size or increasing the thickness of the filter material, the rate of introduction is slowed. Alternatively, an additional barrier that slowly dissolves in water covers the filter material of one of the compartments and delays the introduction of the reagent into the flow of water. In one embodiment, surfactants and buffers are released into the flow of water ahead of sterilizing or disinfecting reagents. This improves the rate of dissolution of the sterilizing or disinfecting reagents in the water. In another embodiment, cleaning compounds are introduced ahead of disinfecting or sterilizing reagents. The cleaning agents begin the removal of adhered organic deposits from the surfaces of instruments to be decontaminated, rendering the surfaces more accessible to the sterilants or disinfectants.

In another embodiment, the cartridge includes a microbial filter 190, as shown in FIG. 3. The microbial filter 190 replaces or supplements the microbe removing filter 22 of the decontamination apparatus A. The incorporation of the microbial filter into a disposable cartridge C ensures that a fresh microbial filter is used for every cycle. The microbial filter 190 is positioned such that all water flowing through the well 16 passes through the microbial filter. The microbial filter preferably filters particles of 2 $\mu$ and above from the fluid passing through the cartridge. Optionally, the filter material of one of the compartments of the cartridge C provides the microbial filter.

Optionally, the microbial filter 190 is impregnated with an antimicrobial composition which is slowly released into the water throughout the cycle. In one embodiment, an encapsulated source of chlorine impregnated into the microbial filter 190 slowly releases active chlorine into the water. A minute quantity of chlorine is sufficient to ensure that any pathogenic microbes entering with the rinse water are killed. Alternatively, the microbial filter 190 is electrically charged. Antimicrobial agents are bound to the filter at charged sites within pores and on surfaces of the filter. These agents are slowly released into solution throughout the cycle. Alternatively, an electrical potential is selectively applied across the microbial filter 190 which causes the agents to be released.

Electrical potentials applied to the filter material of one or other of the compartments may also be employed to control the rate of introduction of the reagents into the fluid.

The filter material is preferably free of additives, such as binders or surfactants, that could be dissolved in the water and contaminate the items to be decontaminated. The material is also preferably lint free, so that small particles of the material do not come away from the second container and become trapped within items to be decontaminated. Further, the material preferably has a fairly high tensile strength and does not disintegrate when it is subjected to a fairly high pressure of water. The material is also preferably unreactive toward the reagents and other additives used in the decontamination unit. A polypropylene nonwoven web having an absolute pore size of under 50 microns, and preferably around 10 microns, is a preferred material because it is virtually lint-free. It also has a high tensile strength, even when under a moderately high water pressure.

The porous nature of the inner container portion and top cover 78 or porous base 58 allows gases formed from the reagents during transit to outgas from the cartridge C.

The preferred reagents include an acid precursor, preferably acetylsalicylic acid and a persalt, preferably sodium perborate. These two reagents are supplied in a sufficient amount to generate peracetic acid in a concentration of 1500 ppm or better with the volume of water used to fill the system and the tray 12. The sodium perborate generates hydrogen peroxide, which, in combination with acetylsalicylic acid as an acetyl donor, forms peracetic acid.

It is also contemplated using powdered reagents which react in a common solvent to generate chlorine gas, hydrogen peroxide, hypochlorous acid, hypochlorites, or other strong oxidants which have biocidal effects.

Preferably, additional corrosion inhibitors, buffers, and a wetting agent are added to these powders. Preferred copper and brass corrosion inhibitors include azoles, benzoates, other five-membered ring compounds, benzotriazoles, tolytriazoles, mercaptobenzothiazole, and the like. Other anti-corrosive buffering compounds include phosphates, molybdates, chromates, dichromates, tungstates, vanadates, other borates, and combinations thereof. These compounds are effective for inhibiting steel and aluminum corrosion. For hard water in which calcium and magnesium salts may tend to precipitate, a sequestering reagent, such as sodium hexametaphosphate is also included.

To assemble the cartridge C of the embodiments shown in FIGS. 4 and 5, the base 58 is first attached to the outer container portion 50. The first reagent is then disposed within the outer container portion. The inner container portion 70 is then placed within the outer container portion with the flange 74 of the inner container portion resting on the flange 54 of the outer container portion. The second reagent is disposed within the inner container portion and the top cover 78 disposed so that it rests on the flange of the inner container portion. The top cover, inner container portion and outer container portion are then sealed together at the flanges of the inner and outer container portions. Thus, the first reagent is sealed within the outer container, while the second reagent is sealed within the inner container. Other methods of assembly are also contemplated. Similar methods of assembly are employed for the other embodiments.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A multi-compartment package for holding powdered reagents which interact with water to form an anti-microbial solution, the package including:
   a) an outer, first container portion including a first peripheral wall which defines a base extending to a continuous side with an opening at an end;
   b) an inner, second container portion including a second peripheral wall which defines a base extending to a continuous side with an opening at an end,
      the first and second container portions being configured such that the second peripheral wall abuts and is connected to the outer first container portion adjacent the end of the first peripheral wall, a top cover covering the openings in the first and second container portions, the first and second peripheral walls being configured such that a first powdered reagent receiving chamber is defined in the first container portion for receiving a first reagent and a second powdered reagent receiving chamber is defined in the second container portion for receiving a second reagent, the first peripheral wall including a region which is formed from a first material which is impermeable to the first reagent but is permeable to water and to solutions containing dissolved reagents, the second peripheral wall including a region which is formed from a second material which is impermeable to the first and second reagents but is permeable to water and to solutions containing dissolved reagents.

2. The package of claim 1, wherein the first container portion end includes a first flange and the second container portion end defines a second flange and wherein the first flange is sealed to the second flange.

3. The package of claim 2, wherein the top cover is sealed to the second flange.

4. The package of claim 2, wherein the first flange is formed from a first polypropylene material, the second flange and top cover are formed from a second polypropylene material, and wherein the second flange and top cover are sealed contemporaneously to the first flange.

5. The package of claim 1, wherein the top cover includes a porous region which is formed from a cover material which is impermeable to the second reagent received in the second container but is permeable to water and to solutions containing dissolved reagents.

6. The package of claim 1, wherein the top cover is formed from a fluid and reagent impermeable material and includes a region which is openable to form an opening for passage of fluids therethrough.

7. The package of claim 1, wherein at least one of the first material and the second material is selected from the group consisting of polypropylene, polyethylene, blended polyolefin non-woven material, porous media, a material which loses its integrity in water, and combinations thereof.

8. The package of claim 7, wherein at least one of the first material and the second material is a spun-bonded polypropylene web having an absolute pore size of under 50 microns.

9. The package of claim 1, wherein the side of the first peripheral wall defines a second opening at a lower end,
   and wherein the base of the first peripheral wall is formed from the first material which is sealed to the side of the first peripheral wall adjacent the lower end to cover the second opening.

10. The package of claim 1, wherein the side of the second peripheral wall defines a second opening at a lower end,
    and wherein the base of the second peripheral wall is formed from the second porous material which is sealed to the side of the second peripheral wall adjacent the lower end to cover the second opening.

11. The package of claim 10, wherein an upper portion of the side of the first peripheral wall provides the side of the second peripheral wall, and wherein the first container portion base includes the first container portion porous region and the second container portion base includes the second container portion porous region.

12. The package of claim 2, wherein the first flange includes an energy director for facilitating sealing of the second flange and top cover to the first flange.

13. The package of claim 12, wherein the energy director includes an upwardly extending annular rib which extends in a ring around a top surface of the first container flange.

14. The package of claim 2, wherein the first container flange includes positioning tabs which extend vertically adjacent an outer edge of the flange.

15. The package of claim 1, further including a microbial filter which filters particles having a size of 2μ or greater from fluids passing through the package.

16. The package of claim 1, wherein the first material allows dissolved reagents to pass through the porous region of the first container portion at a faster rate than the second material allows the dissolved second reagent to pass through the porous region of the second container portion.

17. The package of claim 11 wherein the first reagent includes acetylsalicylic acid and the second reagent includes sodium perborate.

18. The package of claim 1, wherein the first peripheral wall is substantially formed from a non-rigid porous material, the package further including a supporting retainer which retains a shape of the package when the package is wet.

19. A flow-through reagent cartridge for holding powdered reagents which interact with a solvent to form an anti-microbial solution, the cartridge including:
   a) a first reagent receiving compartment which receives a first particulate reagent and is sealed against escape of the first particulate reagent received therein and which selectively releases dissolved reagent;
   b) a second reagent receiving compartment which receives a second particulate reagent and is sealed against escape of the second particulate reagent received therein and which selectively releases dissolved reagent;
      the cartridge being configured for selectively holding the first and second powdered reagents separately within the cartridge and for permitting dissolved first and second reagents to pass out of the cartridge and interact.

20. The cartridge of claim 19, wherein the first and second compartments are stacked and define a fluid flow path through the cartridge, such that solvent is channeled to flow through the first compartment and then through the second compartment.

21. The cartridge of claim 20, wherein the fluid flow path includes a first region of a porous material which allows dissolved reagents to flow out of the first compartment and into the second compartment but which is impermeable to the particulate reagents and a second region of a porous material which allows dissolved reagents to flow out of the second compartment but which is impermeable to the particulate reagents.

22. The cartridge of claim 19, wherein the first and second compartments are side-by-side to define first and second parallel fluid flow paths through the cartridge.

23. The cartridge of claim 22, wherein the first compartment and the second compartment are defined by an outer peripheral wall, a dividing wall, a top cover, and the first and second regions of the porous material, the dividing wall separating the first and second compartments, the top cover being sealed to an upper end of the outer peripheral wall and to a first end of the dividing wall, the first region of the porous material being sealed to a lower end of the outer peripheral wall and to a lower end of the dividing wall to seal the first container against loss of dry reagent, the second region of the porous material being sealed to a lower end of the outer peripheral wall and to a lower end of the dividing wall to seal the second container against loss of dry reagent.

24. The cartridge of claim 23 wherein the first compartment region of filter material differs from the second compartment region of filter material according to a property from the group consisting of thickness, pore size, and combinations thereof.

25. The cartridge of claim 21 further including a source of an antimicrobial composition which slowly releases the antimicrobial composition into fluid passing through the cartridge, the source of the antimicrobial composition being supported on at least one of the regions of the porous material.

26. A multi-compartment package for separately holding a first reagent and a second reagent which react in water to form an anti-microbial solution, the package comprising:
   a first container which holds the first reagent, the first container defining an inlet region through which water is received and an outlet region through which water and dissolved first reagent are discharged;
   a second container which holds the second reagent, the second container defining an inlet region through which water is received and an outlet region through which water and at least dissolved second reagent are discharged; and,
   a porous medium which permits the passage of water, the anti-microbial solution, and water with dissolved first and second reagents, and which blocks the passage of undissolved first and second reagents, the porous medium being disposed at the first container inlet region and at the second container outlet region.

27. The package of claim 26 wherein the second container is disposed within the first container and a common portion of the porous medium separates the first container outlet region and the second container inlet region, such that water with dissolved first reagent flows therethrough into the second container to react with the second reagent.

28. The package of claim 27 wherein
   the second container has a peripheral flange around the inlet region, and
   the first container has a flange that mates with the second container flange.

29. The package of claim 27 wherein at least one of the first and second containers is constructed of the porous medium.

30. An anti-microbial system which receives the package of claim 26 comprising:
   a source of water for applying water at least to the inlet region of the second container;
   a microbial decontamination chamber connected with the first and second container outlet regions for receiving water with dissolved first and second reagents and the anti-microbial solution.

31. A method comprising:
   metering a preselected volume of a first powdered reagent into a first container, the first container including a region of a first porous material which is impermeable to the first reagent but is permeable to water and to aqueous solutions containing dissolved reagents;
   inserting a second container into the first container, the second container including a region of a second porous material which is impermeable to the first reagent and to a second reagent but is permeable to water and to solutions containing dissolved reagents;
   connecting the second container to the first container;
   metering a preselected volume of the second powdered reagent into the second container; and,
   closing the first and second containers.

32. The method of claim 31 further including:
   transporting the containers and the contained powdered reagent to a site at which decontamination is to be performed;

flowing water along a fluid flow path through the first and second containers to dissolve the first and second powdered reagents with water and form a decontamination solution, the fluid flow path including the porous regions of the first and second containers; and, immersing items to be decontaminated in the decontamination solution.

33. The method of claim 31, wherein the first container includes a flange connected to the end of the first container and wherein the second container includes a flange connected to the end of the second container, the first and second containers being configured such that when the second container is inserted into the first container, the second container flange abuts the first container flange, wherein the step of connecting the second container to the first container includes:

connecting the second container flange to the first container flange; and, wherein the step of sealing the top cover over the first and second container open ends includes:

sealing the top cover to the second container flange.

34. The method of claim 33, wherein the steps of connecting the second container flange to the first container flange and sealing the top cover to the second container flange include a sealing method selected from the group consisting of heat welding, ultrasonic welding, glueing, clamping, and combinations thereof.

35. The method of claim 33, wherein the steps of connecting the second container flange to the first container flange and sealing the top cover to the second container flange are carried out concurrently.

36. The method of claim 35, wherein the sealing method includes ultrasonically welding the top cover, second container flange, and first container flange together.

37. The method of claim 36, wherein the first container flange includes an energy director and wherein the sealing method includes:

directing ultrasonic radiation at the energy director to melt the energy director; and pressing the top cover and the second container flange against the first container flange.

38. The method of claim 31, wherein the first peripheral wall is formed from a non-rigid porous material, the method further including:

disposing a retainer within the first container to prevent the peripheral wall from collapsing inward.

39. A decontamination system comprising:

a powdered reagent container receiving well;

a first fluid flow path defined between a water receiving inlet and the reagent container receiving well to bring water from the inlet to the well to mix with powdered reagents and form a decontaminant solution;

a second fluid flow path being defined for the decontaminant solution from the reagent container receiving well to a decontamination region for receiving items to be decontaminated;

a fluid circulator for selectively circulating fluid through the first and second fluid flow paths and among the inlet, the decontamination region, and the reagent container receiving well;

a multi-chamber powdered decontamination reagent holding container for insertion into the well, the container including:

a) an outer, first container portion including a first peripheral wall which defines a first end with an inlet opening and a second end with an outlet opening, the outlet opening being closed with a material which is impermeable to undissolved reagents held in the container and is freely permeable to aqueous solutions;

b) an inner, second container portion including a second peripheral wall which defines a first end with an inlet opening and a second end with an outlet opening the first and second container portions being nested; and c) a top cover covering the first and second container portion inlets.

40. A method of decontamination comprising:

inserting a multi-chamber powdered decontamination reagent holding container into a powdered reagent container receiving well the container including:

a) an outer, first container portion including a first peripheral wall which defines a first end with an inlet opening and a second end with an outlet opening, the outlet opening being closed with a material which is impermeable to undissolved reagents held in the first and second container portions and is freely permeable to aqueous solutions;

b) an inner, second container portion including a second peripheral wall which defines a first end with an inlet opening and a second end with an outlet opening the first and second container portions being nested;

a top cover covering the first and second container portion inlets;

supplying water to the well to mix with powdered reagents and form a decontaminant solution; and, transporting the decontaminant solution to a decontamination region for receiving items to be decontaminated.

* * * * *